US005527903A

United States Patent [19]

Kasori et al.

[11] Patent Number: 5,527,903

[45] Date of Patent: Jun. 18, 1996

[54] PROCESS FOR PREPARING SUCROSE FATTY ACID ESTERS

[75] Inventors: Yukio Kasori; Tetsuro Yamazaki, both of Mie, Japan

[73] Assignee: Mitsubishi Kasei Corporation, Tokyo, Japan

[21] Appl. No.: 897,059

[22] Filed: Jun. 11, 1992

[30] Foreign Application Priority Data

Jun. 14, 1991 [JP] Japan .................................... 3-143542
Jun. 26, 1991 [JP] Japan .................................... 3-154916

[51] Int. Cl.[6] .............................. C07H 1/00; C07H 13/02

[52] U.S. Cl. .......................... 536/115; 536/119; 536/120; 536/124

[58] Field of Search .................................... 536/120, 119, 536/124, 115

[56] References Cited

U.S. PATENT DOCUMENTS

| | | | |
|---|---|---|---|
| 3,951,945 | 4/1976 | Heesen et al. | 536/18.2 |
| 4,591,563 | 5/1986 | Paul et al. | 435/193 |
| 4,954,621 | 9/1990 | Masaoka et al. | 536/119 |
| 4,996,309 | 2/1991 | Matsumoto et al. | 536/124 |
| 5,110,733 | 5/1992 | Kim et al. | 435/183 |

FOREIGN PATENT DOCUMENTS

| | | | |
|---|---|---|---|
| 0319092 | 6/1989 | European Pat. Off. . | |
| 0319091 | 6/1989 | European Pat. Off. . | |
| 320043 | 6/1989 | European Pat. Off. | 536/119 |
| 59-78200 | 5/1984 | Japan . | |
| 61-106589 | 5/1986 | Japan . | |

*Primary Examiner*—Douglas W. Robinson
*Assistant Examiner*—Everett White
*Attorney, Agent, or Firm*—Sughrue, Mion, Zinn, Macpeak & Seas

[57] ABSTRACT

A process for preparing a sucrose fatty acid ester having a low degree of substitution, comprising heat-melting a sucrose fatty acid ester (A) having an average degree of substitution of from 3 to 8 and sucrose or a sucrose fatty acid ester (B) having a lower degree of substitution than that of said sucrose fatty acid ester (A) in the presence of an alkali catalyst and a soap; and a process for preparing a sucrose fatty acid ester having a high degree of substitution comprising a first step of heat-melting a sucrose fatty acid ester (A) having an average degree of substitution of from 3 to 8 and sucrose or a sucrose fatty acid ester (B) having a lower degree of substitution than that of said sucrose fatty acid ester (A) in the presence of an alkali catalyst and a soap and a second step of reacting the resulting molten mixture with a fatty acid lower alkyl ester are disclosed. The invention makes it possible to prepare a sucrose fatty acid ester by a solvent-free method at an increased reaction rate of sucrose while suppressing decomposition of sucrose. Further, the soap used in the reaction can easily be removed from the reaction mixture, and the resulting product is free from coloration.

10 Claims, No Drawings

PROCESS FOR PREPARING SUCROSE FATTY ACID ESTERS

FIELD OF THE INVENTION

This invention relates to a process for preparing a sucrose fatty acid ester of low substitution by using a sucrose fatty acid ester as a part of starting materials under a substantially solvent-free condition. More particularly, it relates to a process for preparing a sucrose fatty acid ester in which a high reaction rate of sucrose can be achieved and the resulting sucrose ester is free from coloration and easy to purify.

BACKGROUND OF THE INVENTION

Sucrose fatty acid esters (hereinafter abbreviated as "SE") are esters formed between sucrose and fatty acids, and their HLB value or other characteristics are subject to variation depending on the degree of substitution on the hydroxyl groups of the sucrose molecule, the carbon atom number of the fatty acid, and so on. They are used chiefly in the field of foodstuffs as emulsifying agents, foaming agents, bacteriostats, or substitutes for edible fats and oils. In particular, sucrose fatty acid esters having an average degree of hydroxyl substitution of 3 or higher, which are lipophilic, have attracted attention as substitutes for edible fats and oils, e.g., spreads, baking fats and oils, and salad oil or as carriers for medical use.

Processes for preparing SE are roughly divided into solvent methods and solvent-free methods. The solvent methods are characterized in that SE can be produced under relatively mild conditions while suppressing formation of by-products due to decomposition of sucrose. The solvent-free methods hold an advantage of simple operation because of no use of any solvent. However, since the ester interchange starts at a high temperature (130° to 160° C.) from the initial stage with the sucrose proportion in the reaction system being high, the reaction involves considerable decomposition of starting materials, such as sucrose. This results in low yield of SE per sucrose and noticeable coloration of the products. In this connection, many proposals on improvement of the solvent-free methods have hitherto been made.

It is known that SE having desired characteristics can be obtained by using other SE species of different characteristics as a part of starting materials according to the solvent-free method. For example, JP-A-59-78200 (the term "JP-A" as used herein means an "unexamined published Japanese patent application") discloses a process in which a mixture of an SE, a soap, and sucrose is melted by heating to obtain an SE having a higher HLB value, i.e., a lower degree of substitution, than that of the starting SE. The disclosure suggests to start with an SE having an HLB value of 3 or more, preferably from 5 to 12. In the working examples of the publication, an SE having an HLB value of 14.0 or 10.5 was prepared by starting with an SE having an HLB value of 10.5 or 7.0, respectively. No case has been reported in which an SE of low substitution is obtained from an SE of high substitution having an HLB value of less than 3 (corresponding to an average degree of substitution of from about 3 to 8).

The soap used as a reaction assistant in a solvent-free method generally has a large carbon atom number and is used in a large quantity. In the working examples of JP-A-59-78200 supra., for instance, a soap having 16 or 18 carbon atoms was used. However, since water solubility of a soap decreases as the carbon atom number increases, easy purification techniques such as liquid-liquid extraction cannot be adopted without difficulty. With respect to the amount of the soap, the publication states that the soap is preferably used in a relatively large amount, e.g., from 100 to 150% by weight based on the starting SE. However, because of the difficulty in removing a soap having a large carbon atom number, use of such a large quantity of a soap leads to economical and operational disadvantages in production on an industrial scale.

On the other hand, it has been proposed to replace the soap with an SE having a different HLB value from the starting SE as a melting assistant to obtain an SE having high degree of substitution. For example, JP-A-61-106589 discloses a process comprising reacting sucrose and a fatty acid lower alkyl ester in a high temperature in the presence of a sucrose fatty acid ester having an average degree of substitution of 3 or more as a melting assistant. In the working example of the publication, sucrose, an SE (sucrose stearate), and a fatty acid lower alkyl ester (methyl stearate) were reacted at a high temperature of 160° C. in the presence of potassium carbonate. According to the example, however, the resulting reaction mixture was brown-tinted and found to contain a by-produced long-chain ($C_{18}$) soap.

While various manipulations have been proposed for purifying the produced SE, none of them is satisfactory. For example, it has been suggested to treat the reaction product with a strongly alkaline aqueous solution followed by centrifugal separation to remove the soap thereby to control the alkali metal ion level below 1 ppm as disclosed in JP-A-1-207296 and JP-A-1-211594. However, fatty acid esters, inter alia, sucrose fatty acid esters, though stable around neutrality, are susceptible to hydrolysis under alkaline or acidic conditions. Further, the above-described alkali treatment tends to induce coloration (caramelization) due to, for example, release of hydroxyl groups from sucrose molecules, forming colored furan compounds (e.g., furfural, furfuryl alcohol). This requires an additional purification step such as decoloring, resulting in a great economical and operational disadvantage in industrial production.

SUMMARY OF THE INVENTION

An object of the present invention is to provide a solvent-free process for preparing an SE with high efficiency while preventing decomposition of sucrose and achieving a high reaction rate of sucrose.

Another object of the present invention is to provide a solvent-free process for preparing an SE in which a soap can be removed easily from the reaction system and the product can be purified easily.

Other objects and effects of the present invention will be apparent from the following description.

As a result of extensive investigations, the inventors have found that an SE of low substitution can be efficiently prepared by starting with an SE of high substitution having an average degree of substitution of from 3 to 8.

It has also been found that an SE of high substitution can be efficiently prepared by applying the above-described process to a two-stage reaction system.

The present invention has been completed based on these findings.

A first embodiment of the present invention relates to a process for preparing an SE having a low degree of substitution (hereinafter referred to as SE-C), comprising heat-melting an SE having an average degree of substitution of from 3 to 8 (hereinafter referred to as SE-A) and sucrose or an SE having a lower degree of substitution than that of SE-A (hereinafter referred to as SE-B) in the presence of an alkali catalyst and a soap.

A second embodiment of the present invention relates to a process for preparing an SE having a high degree of substitution, comprising a first step of heat-melting SE-A and sucrose or SE-B in the presence of an alkali catalyst and a soap; and a second step of reacting the resulting molten mixture with a fatty acid lower alkyl ester.

DETAILED DESCRIPTION OF THE INVENTION

SE-A and SE-B which can be used in the present invention are not limited by kind of fatty acid moieties or process of production. Examples of suitable fatty acids to be used for preparing these SE's include saturated or unsaturated fatty acids having from 6 to 24 carbon atoms, and preferably from 12 to 22 carbon atoms, e.g., lauric acid, myristic acid, palmitic acid, stearic acid, oleic acid, erucic acid, etc., and mixtures thereof.

SE-A generally has an average degree of substitution of from 3 to 8 (corresponding to an HLB value of from 0 to 3), and preferably from 4 to 8 (corresponding to an HLB value of from 0 to 2). Specific examples of the SE-A include "S-170" (a mixed sucrose ester having a stearic acid moiety to palmitic acid moiety weight ratio of 70/30 and an average degree of substitution of 5.2) and "P-170" (a mixed sucrose ester having a palmitic acid moiety to stearic acid moiety weight ratio of 70/30 and an average degree of substitution of 5.3), both produced by Mitsubishi Kasei Corporation.

The average degree of substitution of SE-B is not particularly limited as long as it is lower than that of SE-A, and generally ranges from 0.1 to 2 (corresponding to an HLB value of from 5 to 20), and preferably from 1 to 1.7 (corresponding to an HLB value of from 8 to 17). Specific examples of the SE-B include "P-1670" (a mixed sucrose ester having a palmitic acid moiety to stearic acid moiety weight ratio of 70/30 and an average degree of substitution of 1.3) and "S-1170" (a mixed sucrose ester having a stearic acid moiety to palmitic acid moiety weight ratio of 70/30 and an average degree of substitution of 1.6), both produced by Mitsubishi Kasei Corporation.

The ratio of SE-A to sucrose or SE-B to be charged is not particularly limited and subject to variation depending on the desired degree of substitution of SE-C. For example, SE-A is generally used in an amount of from 10 to 90% by weight, and preferably from 30 to 85% by weight, more preferably from 50 to 85% by weight, based on the total reaction mixture (total amount of SE-A, SE-B, sucrose, soap and catalyst), and sucrose or SE-B is generally used in an amount of from 1 to 90% by weight, and preferably from 10 to 60% by weight, on the same basis. Where the heat-melting reaction is carried out in a low temperature of 110° C. or less, because the reaction mixture is apt to have an increased viscosity, it is preferable to use SE-A in an amount larger than sucrose or SE-B. Further, SE-B is preferable to sucrose for maintaining the viscosity of the reaction mixture low.

The alkali serving as a catalyst is selected appropriately from alkali metal hydroxides (e.g., potassium hydroxide, sodium hydroxide, lithium hydroxide), alkali metal carbonates (e.g., potassium carbonate, sodium carbonate, lithium carbonate), and alkali metal alkoxides (e.g., sodium methoxide, sodium ethoxide, potassium methoxide).

The alkali catalyst is used in an amount generally of from 0.01 to 1 mol, and preferably from 0.1 to 0.5 mol, per mol of sucrose or SE-B. The catalyst to be supplied may have any form. For example, it may be supplied in a powdered form or as dissolved in water or an alcohol. It is preferable to previously activate the catalyst by uniformly dissolving it in water and/or a lower alcohol together with sucrose or SE-B, a soap, etc., followed by drying in reduced pressure to remove the water and/or lower alcohol.

In carrying out the activation, the amounts of water and/or a lower alcohol, the catalyst, sucrose or SE-B, and the soap to be charged and the manner of charging them are not particularly limited. Preferred examples of the lower alcohol to be used includes those miscible with water at an arbitrary ratio, such as methyl alcohol, ethyl alcohol, and butyl alcohol. The amount of water and/or the lower alcohol is so adjusted that the mixture of the above-described components may be dissolved completely and uniformly. The water and/or lower alcohol is removed by drying at an inner temperature generally of from 20° to 100° C., and preferably of from 40° to 80° C., under atmospheric pressure or reduced pressure. For complete removal of water, drying may more preferably be effected in vacuo (1 Torr or less) at a temperature of from 40° to 80° C. Any drying apparatus may be used. For example, a spray drier commonly employed for drying of powder is preferably used.

The soap which can be used in the present invention is not limited and preferably includes alkali metal or alkaline earth metal salts of carboxylic acids having from 2 to 10 carbon atoms, and particularly 3 to 8 carbon atoms. The amount of the soap to be used generally ranges from 0.1 to 90% by weight, and preferably from 1 to 50% by weight, based on the amount of SE-A, or generally of from 1 to 30% by weight, and preferably from 3 to 15% by weight, based on the total reaction mixture. The soap is added in the form of powder or as dissolved in water and/or a lower alcohol. It is recommended that sucrose or SE-B, the catalyst, and the soap are previously dissolved in water and/or a lower alcohol uniformly, and the solvent is removed by distillation and drying to obtain an activated substance as described above.

The kind and amount of the soap to be used are greatly concerned with the HLB values and the amounts of SE-A and sucrose or SE-B used. In general, according as the HLB value (i.e., hydrophilic properties) of the whole reaction system becomes higher, it is preferable to use a soap having a shorter chain length, i.e., higher hydrophilic properties, and according as the chain length of the soap becomes shorter, the requisite amount thereof tends to be reduced. For example, in the case of using SE-A having an HLB value of 1 and sucrose, it is preferable to use potassium caproate (carbon atom number: 6) in an amount of from 10 to 20% by weight based on SE-A. In the case of using SE-A having an HLB value of 2 and sucrose, it is preferable to use potassium butyrate (carbon atom number: 4) or potassium propionate (carbon atom number: 3) in an amount of from 5 to 10% by weight based on SE-A.

Heat-melting of the reaction system is carried out at a temperature ranging generally from 50° to 140° C., and preferably from 80° to 110° C., under a pressure generally of from 0.01 Torr to atmospheric pressure, and preferably from 0.1 to 500 Torr. While not limiting, the apparatus to be used for melting includes generally employed stirring type apparatus and a kneader or extruder used for highly viscous mixtures. The order of addition of starting materials is not particularly restricted, but it is recommended that SE-A is first melted at a prescribed temperature and then sucrose or SE-B is added thereto. In this case, sucrose or SE-B is preferably used in the form of powder ground as finely as possible for achieving uniform mixing and rapid melting. The period of the heat-melting time is usually in the range of from 0.5 to 8 hours, preferably from 1 to 4 hours.

The reaction rate of sucrose is generally controlled between 20 and 80%, and preferably between 30 to 70%.

The thus produced SE-C may be isolated in any means, for example, liquid-liquid extraction. Liquid-liquid extraction can be carried out by first adding an organic acid (e.g., lactic acid, acetic acid, succinic acid) to the reaction mixture to deactivate the catalyst and then adding an organic solvent and/or water as an extracting solvent. Any organic solvent can be used as long as it is capable of dissolving an SE. Examples of suitable organic solvents include lower alcohols, e.g., isopropyl alcohol and isobutyl alcohol. By the liquid-liquid extraction, the soap is dissolved in the aqueous layer and thus removed so that the final product has an extremely reduced soap concentration. The thus recovered soap can be reused as a reaction assistant, giving an economical merit.

The second embodiment of the present invention comprises two reaction steps, the first step corresponding to the above-described heat-melting reaction between SE-A and sucrose or SE-B.

Where sucrose is used, the reaction system at the end of the first step has an increased SE concentration and a decreased sucrose concentration as a result of the reaction between SE-A and sucrose. While the reaction rate of the first step varies depending on the carbon atom number of the soap used, the reaction rate of sucrose in the first step is generally controlled between 20 and 80%, and preferably between 30 and 70%. Where SE-B is used in the first step, the reaction proceeds between SE-A and SE-B similarly to the case of using sucrose.

In the second step, a fatty acid lower alkyl ester is added to the molten mixture obtained in the first step to induce an ester interchange reaction thereby producing an SE having an increased average degree of substitution, i.e., from 3 to 8 (hereinafter referred to as "SPE").

Any kind of fatty acid lower alkyl esters can be used without limitation of the constituting fatty acid or the preparation process. Esters between one or more saturated and/or unsaturated fatty acids having from 6 to 24 carbon atoms, and preferably from 12 to 22 carbon atoms, and a lower alcohol, e.g., methanol, ethanol, and propanol, are preferably used. Specific examples thereof include methyl stearate and methyl palmitate. The amount of the fatty acid lower alkyl ester to be added is selected arbitrarily according to the desired average degree of substitution of SPE, for example, 50 to 500% by weight, preferably 100 to 350% by weight, based on the total reaction mixture obtained in the first step.

The fatty acid lower alkyl ester may be added to the molten mixture obtained in the first step all at once, continuously, or in divided portions. Where the reaction rate of sucrose achieved in the first step is low, that is, the molten reaction mixture has a high sucrose concentration, the fatty acid lower alkyl ester is preferably added continuously or in divided portic..s so as not to destroy the emulsion state of the reaction system. If a large quantity of the fatty acid lower alkyl ester is added all at once to the reaction system having a high sucrose concentration, the sucrose and soap remaining in the reaction system tend to be agglomerated, resulting in a reduction of the sucrose reaction rate finally reached.

The reaction of the second step is effected usually at a temperature of from 80° to 180° C. under a pressure of from 0.01 to 50 Torr, and preferably at a temperature of from 100° to 180° C. under a pressure of from 0.01 to 20 Torr. In order to minimize coloration of the final product and to stabilize the emulsion state of the reaction system in the initial stage of the second step (i.e., at the time of addition of a fatty acid lower alkyl ester), it is desirable to change the reaction conditions in two or more stages in such a manner that the reaction be conducted under relatively mild conditions within the above-recited ranges until the reaction rate of thermally labile sucrose reaches 80 to 100% and, thereafter, the temperature is elevated and/or the pressure is reduced within the above-described ranges. While the manner of changing the reaction conditions is not particularly restricted, the temperature elevation and/or pressure diminution is preferably effected continuously or stepwise so that the thermally labile sucrose or sucrose fatty acid ester of low substitution may be prevented from being decomposed or colored.

The thus produced SPE can be purified in the same manner as in the first embodiment of the present invention.

The present invention is now illustrated in greater detail with reference to certain specific examples provided herein, but it should be understood that the present invention is not construed as being limited thereto. All the percents and parts are given by weight unless otherwise indicated.

In the examples, a residual sucrose content in the reaction mixture obtained was determined by dissolving a sample in dimethylformamide to convert sucrose to its trimethylsilyl derivative which was then analyzed by gas chromatography.

The produced SE in the reaction mixture was analyzed by adding tetrahydrofuran to a sample, removing any insoluble matter by filtration, and subjecting the filtrate to gel-permeation chromatography and reverse phase high performance liquid chromatography.

EXAMPLE 1

1) Pretreatment for Activation

In a 1 l-volume round flask equipped with a stirrer were charged 47.4 g of sucrose, 1.83 g of potassium hydroxide as a catalyst, and 19.7 g of potassium caproate (carbon atom number: 6) as a soap. Then, 50 g of water and 300 g of methanol were added thereto to form a uniform solution. The solvent was removed by nitrogen stripping while maintaining the inner temperature at 55° to 60° C. The residue was dried in vacuo (0.1 Torr or lower) for 4 hours to obtain an adduct in the form of fine powder.

2) Heat-Melting Reaction

To the flask was added 120 g of S-170 (sucrose stearate of high substitution, produced by Mitsubishi Kasei Corporation; average degree of substitution: 5.2) as SE-A, and the mixture was allowed to react at 100° C. and 1 Torr for 3 hours. The amount of the soap charged corresponded to 10.4% based on the total reactants.

The results of analyses on the resulting highly viscous mixture revealed that the sucrose reaction rate as calculated from the residual sucrose concentration was 64.1%; the yield of the produced SE was 76.9% (based on the whole reaction mixture); and the average degree of substitution of the SE was 2.5. These results are shown in Table 1 below.

3) Purification of SE

Ten parts of the resulting reaction mixture were neutralized with lactic acid and dissolved in a mixed solvent of 90 parts of isobutyl alcohol and 100 parts of water, followed by stirring at 60° C. for 10 minutes. After allowing the mixture to stand for 15 minutes, the isobutyl alcohol layer containing the produced SE and the aqueous layer containing the unreacted sucrose, soap, etc. were separated from each other. The isobutyl alcohol layer was concentrated under reduced pressure to recover a purified SE as a white solid almost quantitatively.

The potassium ion concentration of the reaction mixture (before liquid-liquid extraction) as determined by titration was 6.78 mmol while that of the purified SE was found to be 0.59 mmol, indicating a rate of potassium ion removal of 91.3%.

EXAMPLES 2 TO 7

The same procedure as in Example 1 was repeated, except for changing the kind of the soap as shown in Table 1. The results of the reaction are also shown in Table 1.

TABLE 1

| Example No. | Soap Kind | Soap Carbon Atom Number | Sucrose Reaction Rate (%) | Yield of SE (%) | Average Degree of Substitution of SE-C |
|---|---|---|---|---|---|
| 1 | Potassium caproate | 6 | 64.1 | 79.6 | 2.5 |
| 2 | Potassium butyrate | 4 | 41.1 | 73.8 | 3.0 |
| 3 | Potassium caprylate | 8 | 37.5 | 72.9 | 3.4 |
| 4 | Potassium propionate | 3 | 27.8 | 70.5 | 3.6 |
| 5 | Potassium acetate | 2 | 7.1 | 65.3 | 4.7 |
| 6 | Potassium benzoate | 7 | 30.8 | 71.2 | 3.4 |
| 7 | Potassium stearate | 18 | 25.3 | 69.7 | 3.8 |

EXAMPLES 8 AND 9

The same procedure as in Example 2 was repeated, except for changing the amount of the soap (potassium butyrate) as shown in Table 2 below. The results of the reaction are shown in Table 2. The results of Example 2 are also shown for better understanding.

TABLE 2

| Example No. | Amount of Soap (%) | Sucrose Reaction Rate (%) | Yield of SE (%) | Average Degree of Substitution of SE-C |
|---|---|---|---|---|
| 2 | 10.4 | 41.1 | 73.8 | 3.0 |
| 8 | 5.0 | 40.3 | 73.3 | 3.1 |
| 9 | 2.5 | 12.2 | 66.5 | 4.5 |

EXAMPLES 10 TO 12

The same procedure as in Example 1 was repeated, except for changing the method for pretreating the sucrose, alkali catalyst, and soap as described below. The results of the reaction are shown in Table 3 below. The results of Example 1 are also shown for better understanding.

EXAMPLE 10

Only sucrose and the soap were uniformly dissolved and dried in vacuo. Potassium carbonate ($K_2CO_3$) as a catalyst was added in the form of powder. The amount of potassium carbonate added was a half of the mols of potassium hydroxide (KOH) used in Example 1.

EXAMPLE 11

All of sucrose, soap, and potassium hydroxide were added in the form of powder (non-activated).

EXAMPLE 12

Only sucrose and potassium hydroxide as a catalyst were uniformly dissolved and dried in vacuo. The soap was added in the form of powder.

TABLE 3

| Example No. | Pretreatment of Sucrose* (%) | Sucrose Reaction Rate (%) | Yield of SE (%) | Average Degree of Substitution of SE-C |
|---|---|---|---|---|
| 1 | (FS+KOH+Soap) | 64.1 | 79.6 | 2.5 |
| 10 | (FS+Soap)+$K_2CO_3$ | 48.1 | 75.6 | 2.7 |
| 11 | FS+$K_2CO_3$+Soap | 31.2 | 70.5 | 3.3 |
| 12 | (FS+KOH)+Soap | 18.7 | 68.2 | 3.8 |

Note:
*FS: Sucrose
The components in the parentheses were activated.

EXAMPLES 13 AND 14

The same procedure as in Example 8 was repeated, except for changing the average degree of substitution of SE-A as shown in Table 4 below. The results obtained are also shown in the Table together with the results of Example 8.

TABLE 4

| Example No. | SE-A Average Degree of Substitution | SE-A HLB Value | Sucrose Reaction Rate (%) | Yield of SE (%) | Average Degree of Substitution of SE-C |
|---|---|---|---|---|---|
| 8 | 5.2 | 1 | 40.3 | 73.3 | 3.1 |
| 13 | 6.3 | 0 | 24.5 | 69.7 | 3.5 |
| 14 | 3.9 | 2 | 20.5 | 68.6 | 2.8 |

COMPARATIVE EXAMPLE 1

The same procedure as in Example 8 was repeated, except for using SE-A having an average degree of substitution of 2.2 (corresponding to an HLB value of 3). As a result of analyses, the sucrose reaction rate reached was 9.3%; the yield of the SE was 65.6%; and the average degree of substitution was 2.0; indicating much poor reaction efficiency in comparison to Example 8. Further, the reaction mixture was in a uniform starchy state of high viscosity from the initial stage. The high viscosity became a stirring rate-determining step in a general stirrer, making the reaction difficult.

EXAMPLE 15

The same procedure as in Example 1 was repeated, except for replacing potassium caproate with an equimolar amount of potassium stearate (corresponding to 19.6% of the total reactants). As a result of analyses, the sucrose reaction rate was 45.6%, and the SE had a yield of 68.1% and an average degree of substitution of 3.0. The reaction mixture was worked-up in the same manner as in Example 1 to obtain a purified SE as a white solid.

The potassium ion concentration of the reaction mixture (before liquid-liquid extraction) was 6.08 mmol while that of the purified SE was found to be 3.44 mmol, indicating a rate of potassium ion removal of 43.4%.

EXAMPLE 16

The same procedure as in Example 11 was repeated, except for replacing sucrose with the same weight of S-1670 (sucrose monostearate produced by Mitsubishi Kasei Corporation; average degree of substitution: 1.3) as SE-B. The proportion of the SE having a degree of substitution of from 2 to 4 in the total SE (SE-A+SE-B) was 39% before the reaction but was found to be increased to 72% after the reaction. The average degree of substitution of the SE in the reaction mixture was 3.2.

EXAMPLE 17

First Step

The same reaction as in Example 1 was carried out to obtain a molten mixture.

Second Step

To an about 190 g aliquot of the molten mixture was added 211.4 g of methyl stearate, and the mixture was allowed to further react at 100° C. and 1 Torr for 8 hours. A sampling taken at this point was analyzed. The results of analyses are shown in Table 5 below.

For the purpose of further increasing the average degree of substitution, the reaction was further continued for an additional period of 8 hours under conditions of 130° C. and 0.1 Torr. The results of analyses on the resulting reaction mixture are also shown in Table 5. The reaction mixture was worked-up in the same manner as in Example 1 to recover a purified SE as a white solid almost quantitatively.

COMPARATIVE EXAMPLE 2

The same procedure as in Example 17 was repeated, except that the methyl stearate was added at the beginning of the first step, and the reaction was continued for an overall period of 9 hours. The results of analyses are shown in Table 5.

COMPARATIVE EXAMPLE 3

In a 1 l-volume round flask equipped with a stirrer was charged 120 g of S-170 and heated at 60° to 70° C. Then, 47.4 g of sucrose fine powder, 19.7 g of potassium caproate, 1.91 g of potassium carbonate, and 211.4 g of methyl stearate were added thereto. The mixture was allowed to react at 100° C. and 1 Torr for 9 hours. A sampling taken at this point was analyzed. The results of analyses are shown in Table 5.

Further, for the purpose of further increasing the average degree of substitution, the reaction was further continued for an additional period of 8 hours under conditions of 130° C. and 0.1 Torr. The results of analyses are shown in Table 5.

COMPARATIVE EXAMPLE 4

Sucrose was activated by pretreatment in the same manner as in Example 1. In the flask was charged 211.4 g of methyl stearate without adding SE-A, and the mixture was allowed to react at 100° C. and 1 Torr for 9 hours. The resulting reaction mixture was comprised of masses of black brown balls compound of sucrose and potassium caproate, and methyl stearate in a dissolved state. The results of analyses on the resulting reaction mixture are shown in Table 5. The reaction rate of methyl stearate as calculated from the amount of the methanol distillate was 0.4%. Production of SPE could not be confirmed.

EXAMPLE 18

Sucrose was activated in the same manner as in Example 1, except for using 9.4 g of potassium butyrate (carbon atom number: 4) as a soap.

The same procedure as in Example 17 was repeated, except that the amount of S-170 used in the first step was changed to 126.6 g, the reaction of the first step was continued for 5 hours, the amount of methyl stearate added in the second step was changed to 223.0 g, and the reaction of the second step was continued for 4 hours. The reaction conditions were not changed during the second step, and further reaction to increase the degree of substitution was not changed. The results of analyses on the resulting reaction mixture are shown in Table 5.

COMPARATIVE EXAMPLE 5

The same procedure as in Comparative Example 3 was repeated, except for using 9.4 g of potassium butyrate as a soap. The reaction was continued for 9 hours without changing the conditions. The results of analyses are shown in Table 5.

COMPARATIVE EXAMPLE 6

The same procedure as in Comparative Example 4 was repeated, except for using 9.4 g of potassium butyrate as a soap. The results of analyses are shown in Table 5. The resulting reaction mixture was comprised of brown balls of sucrose, masses of potassium caproate, and methyl stearate in a dissolved state. No by-produced methanol distillate was observed, and no SPE was detected in the reaction mixture.

EXAMPLE 19

The same procedure as in Example 17 was repeated, except for using 19.7 g of potassium caprate (carbon atom number: 8) as a soap, continuing the reaction of the first step for 5 hours, and continuing the reaction of the second step for 4 hours. The conditions were not changed during the second step, and further reaction to increase the degree of substitution was not conducted. The results of analyses on the resulting reaction mixture are shown in Table 5.

TABLE 5

| Example No. | Carbon Atom Number of Soap | Sucrose Reaction Rate (%) | Fatty Acid Methyl Ester Reaction Rate (%) | Yield of SPE (%) | Average Degree of Substitution of SPE | Tone of SPE |
|---|---|---|---|---|---|---|
| Example 17* | 6 | 98.3 | 39.1 | 59.9 | 4.0 | pale yellow |
| | | 100.0 | 94.2 | 92.6 | 5.6 | pale brown |
| Example 18 | 4 | 82.1 | 24.1 | 52.4 | 3.7 | pale yellow |
| Example 19 | 8 | 95.3 | 24.7 | 52.1 | 3.0 | pale yellow |
| Comparative Example 2 | 6 | 69.2 | 48.4 | 60.9 | 4.4 | deep brown |
| Comparative Example 3* | 6 | 52.9 | 30.9 | 50.7 | 4.2 | black brown |
| | | 86.3 | 80.2 | 77.8 | 4.9 | black |
| Comparative Example 4 | 6 | 0 | 0.4 | 0 | — | — |
| Comparative Example 5 | 4 | 48.7 | 25.7 | 49.2 | 4.1 | deep brown |
| Comparative Example 6 | 4 | 0 | 0 | 0 | — | — |

Note:
*In Example 17 and Comparative Example 3, the data in the lower column are for the reaction further conducted at an elevated temperature under reduced pressure for 8 hours.

As described and demonstrated above, the process according to the present invention makes it possible to prepare a sucrose fatty acid ester by a solvent-free method at an increased reaction rate of sucrose while suppressing decomposition of sucrose. Further, the soap used in the reaction can easily be removed from the reaction mixture, and the resulting product is free from coloration.

While the invention has been described in detail and with reference to specific examples thereof, it will be apparent to one skilled in the art that various changes and modifications can be made therein without departing from the spirit and scope thereof.

What is claimed is:

1. A process for preparing a sucrose fatty acid ester (C), said process comprising the steps of:

(1) uniformly dissolving sucrose, alkali catalyst and a soap which is an alkali metal salt of a carboxylic acid having from 3 to 8 carbon atoms in water and/or a lower alcohol, followed by drying to obtain a substance containing activated sucrose;

(2) heat-melting said substance and a sucrose fatty acid ester (A) having an average degree of substitution of from 4 to 8 at a temperature of from 50° to 140° C., so as to form said sucrose fatty acid ester (C) having a lower average degree of substitution than that of said sucrose fatty acid ester (A); and (3) isolating said sucrose fatty acid ester (C) by liquid-liquid extraction wherein said soap is dissolved in an aqueous layer;

wherein said soap in said step (1) is used in an amount of from 0.1 to 90% by weight based on said sucrose fatty acid ester (A).

2. A process as claimed in claim 1, wherein said sucrose fatty acid ester (A) is used in an amount of from 10 to 90% by weight based on the total reaction mixture.

3. A process as claimed in claim 1, wherein said soap is used in an amount of from 1 to 30% by weight based on the total reaction mixture.

4. A process as claimed in claim 1, wherein in step (2) the sucrose has a rate of reaction from 20 to 80%.

5. A process for preparing a sucrose fatty acid ester (E), said process comprising the steps of:

(1) uniformly dissolving sucrose, alkali catalyst and a soap which is an alkali metal salt of a carboxylic acid having from 3 to 8 carbon atoms in water and/or a lower alcohol, followed by drying to obtain a substance containing activated sucrose;

(2) heat-melting said substance and a sucrose fatty acid ester (A) having an average degree of substitution of from 4 to 8 at a temperature of from 50° to 140° C. to obtain a molten mixture;

(3) reacting said molten mixture with a fatty acid lower alkyl ester, so as to form said sucrose fatty acid ester (E) in an amount greater than the amount of sucrose fatty acid ester (A) that is heat-melted in said step (2); and (4) isolating said sucrose fatty acid ester (E) by liquid-liquid extraction wherein said soap is dissolved in an aqueous layer;

wherein said soap in said step (1) is used in an amount of from 0.1 to 90% by weight based on said sucrose fatty acid ester (A).

6. A process as claimed in claim 5, wherein said sucrose fatty acid ester (A) is used in an amount of from 10 to 90% by weight based on the total reaction mixture.

7. A process as claimed in claim 5, wherein said soap is used in an amount of from 1 to 30% by weight based on the total reaction mixture.

8. A process as claimed in claim 5, wherein in said step (2) the sucrose has a rate of reaction of from 20 to 80%.

9. A process as claimed in claim 5, wherein the reaction of step (3) is carried out at a temperature of from 80° to 180° C. and under a pressure of from 0.01 to 50 Torr.

10. A process as claimed in claim 5, wherein the reaction of the step (3) is carried out in such a manner that temperature is elevated within a range of from 100° to 180° C. and/or the pressure is diminished within a range of from 0.01 to 20 Torr until the point when the reaction rate of sucrose reaches 80 to 100%.

* * * * *